United States Patent [19]
Andresen

[11] Patent Number: 5,722,093
[45] Date of Patent: Mar. 3, 1998

[54] HIP PROTECTOR

[75] Inventor: Susanne Hamann Andresen, Espergærde, Denmark

[73] Assignee: Sahva A/S, Copenhagen, Denmark

[21] Appl. No.: 676,269

[22] PCT Filed: Jan. 5, 1995

[86] PCT No.: PCT/DK95/00004

§ 371 Date: Jul. 8, 1996

§ 102(e) Date: Jul. 8, 1996

[87] PCT Pub. No.: WO95/19154

PCT Pub. Date: Jul. 20, 1995

[30] Foreign Application Priority Data

Jan. 17, 1994 [DK] Denmark .................. 9400025

[51] Int. Cl.⁶ .................. A41D 13/00; A41D 27/26
[52] U.S. Cl. .................. 2/23; 2/455; 2/22; 2/267
[58] Field of Search .................. 2/22, 24, 267, 2/2, 23, 455

[56] References Cited

U.S. PATENT DOCUMENTS

| | | | |
|---|---|---|---|
| 1,786,268 | 12/1930 | Snavely | 2/2 |
| 2,320,705 | 6/1943 | Reynolds | 2/2 |
| 2,481,291 | 9/1949 | Coleman | 2/2 |
| 3,044,075 | 7/1962 | Rawlings | 2/267 |
| 3,607,601 | 9/1971 | Milam, Jr. et al. | 161/159 |
| 4,373,211 | 2/1983 | Goudreau et al. | 2/2 |
| 4,441,211 | 4/1984 | Ponzis | 2/2 |
| 4,573,216 | 3/1986 | Wortberg | 2/2 |
| 4,807,301 | 2/1989 | Ferber | 2/2 |
| 5,105,473 | 4/1992 | Valtakari | 2/267 |
| 5,497,511 | 3/1996 | Zade | 2/267 |

FOREIGN PATENT DOCUMENTS 2150489   10/1971   Germany.
8603019    6/1986   Germany.

*Primary Examiner*—Bibhu Mohanty
*Attorney, Agent, or Firm*—Dick and Harris

[57] ABSTRACT

A hip protector (4) comprising a dome-shaped element having a concave side adapted to be attached to the hip region of a human body (1). The hip protector is formed in the shape of a curved shell made of foamed rigid plastic material. The protector can be attached to the inner side of an underwear (2), such as an inner pocket (3), for correct positioning.

11 Claims, 5 Drawing Sheets

HIP PROTECTOR

FIELD OF THE INVENTION

This invention relates to improvements in the dome-shaped rigid hip protector with an inwardly curved surface adapted to fit the hip of the human body.

BRIEF DESCRIPTION OF THE PRIOR ART

The known hip protector comprises a dome-shaped rigid plate member which is made of, for example, a plastic material and is generally oblong in plane view and a lining having cushioning properties as made of a foam rubber or the like material.

Research and trials using the known hip protector revealed that the protector prevents or drastically reduces the incidence of bone fracture or other injury associated with falling, especially fracture of the hip bones and neck of the femur in elderly or physically debilitated persons. This is because the external forces applied to the local bone are spread over a large area. Of course, the hip protector can also be worn by sportsmen, typically handball or ice hockey players, to protect themselves against abrasion wounds and bone fractures.

The said research and trials were performed with the hip protector attached to the user's clothes, especially the inner side of his pants or underwear. The results revealed that in order that the hip protector may function properly, it is of paramount importance to position the hip protector in exact anatomical position with fairly high precision.

The known hip protector includes a dome-shaped rigid plate member and a cushioning member or lining on the concave side of said plate member. The cushioning member comprises parts which are glued together. This structure involves a fairly high cost of manufacture, as it consists of parts being assembled during the course of manufacture. Moreover, as found by use trials, the said structure does not withstand laundering at a temperature over 30° C. which is the usual treatment of cottons, for example cotton underwear, among other things because the cushioning member tends to come apart at the glueings.

SUMMARY OF THE INVENTION

The hip protector of this invention comprises a dome-shaped element including an inwardly concave side which is adapted to fit the hip of a human body. The hip protector includes a domed tough and solid shell, and its entire surface is made of a foamed rigid thermoplastic material. The hip protector provides for a series of substantial economic and practical advantages. Thus the hip protector can be manufactured on a mass production scale by the modern production technology. Moreover, this hip protector is extremely lightweight which is a great advantage to the user. Furthermore, the protector can withstand ordinary cleaning and can for example be safely laundered at a temperature over 30° C. as attached to the user's specially made underwear which is used to position the protector correctly on the body.

The hip protector of this invention, in a preferred embodiment, comprises a shell made of a closed-cell thermoplastic material such as polypropylene foam. The closed-cell surfaces can be easily cleaned and do not easily pick up dirt.

The hip protector of this invention preferably includes a substantially uniform thickness and has an annular, rounded rim. Further, the shell includes an internal reinforcing core.

The core, preferably comprises a curved member made of a rigid thermoplastic material such as polypropylene and is completely concealed in the shell.

In another preferred embodiment, the shell comprises a substantially elliptical or oval element with a major diameter that terminates in a generally round end and a slightly obtuse end. In such an embodiment the major diameter measures between 13 cm and 18 cm, preferably 16 cm; a minor diameter measures between 9 cm and 14 cm, preferably 11.5 cm; and a thickness measures between 0.5 cm and 1.5 cm, preferably 0.9 cm.

In yet another preferred embodiment, the hip protector is formed to fit the neck of the femur with its slightly obtuse end facing downward as attached and the hip protector is curved to provide a depth of 2.5 to 4.5 cm, preferably 3.0 cm.

With the above-described dimensions the hip protector is capable of fitting a large number of persons. For special uses it will naturally be convenient to provide the hip protector in different sizes, but preferably this special use hip protector will utilize the above-identified measurements with respect to general proportions and shape.

The hip protector, in another embodiment, includes a grained surface and a plurality of apertures extending from the concave side to the convex side at a distance from the rim of the shell. The grained surface is comfortable to the user and aids in keeping the hip protector in the correct position. A preferred hip protector may be attached to the inner side of clothing equipped with pockets, preferably inner pockets, which receive the hip protector for the correct positioning of the hip protector. In such a preferred embodiment, the clothing may comprise for example a knitted underwear, which is very convenient in use.

BRIEF DESCRIPTION OF THE DRAWINGS

This invention is now described in detail with reference to the embodiments illustrated in the drawings. In the drawings.

DETAILED DESCRIPTION OF THE DRAWINGS

FIGS. 2 through 7 are substantially life-sized views of the hip protector 4 of this invention.

Figure 1:
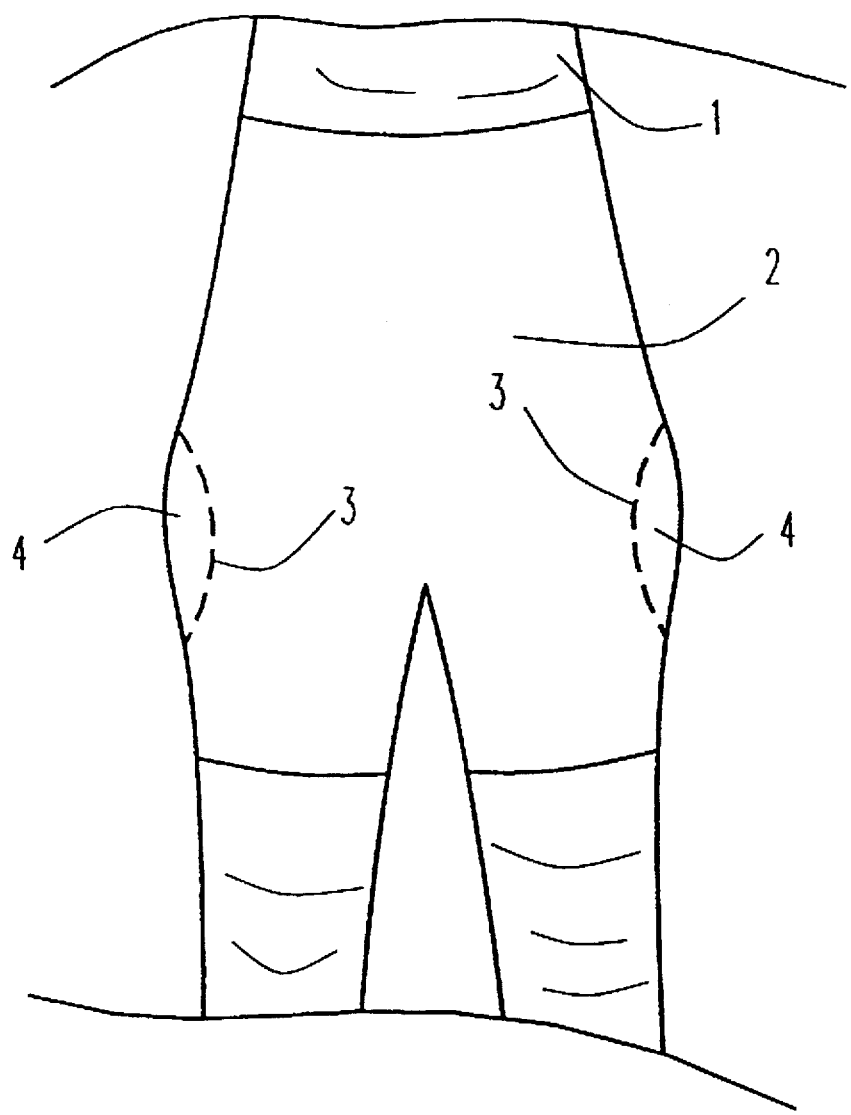
FIG. 1 shows, in sketch, a hip protector attached to a human body.

FIG. 1 is a partial view of a human body 1 wearing an underwear 2 provided with a pocket 3 at either side in the region corresponding to the neck of the femur. Accommodated in each pocket is the hip protector of this invention as will be described in detail with reference to FIGS. 2 through 7.

The hip protector 4 comprises a closed-cell solid thermoplastic shell 5 which is configured as shown in FIGS. 2 through 5. This thermoplastic shell 5 may for example be made of polypropylene. As illustrated, it has a rounded rim 9 and is substantially uniform in thickness.

Figure 2:
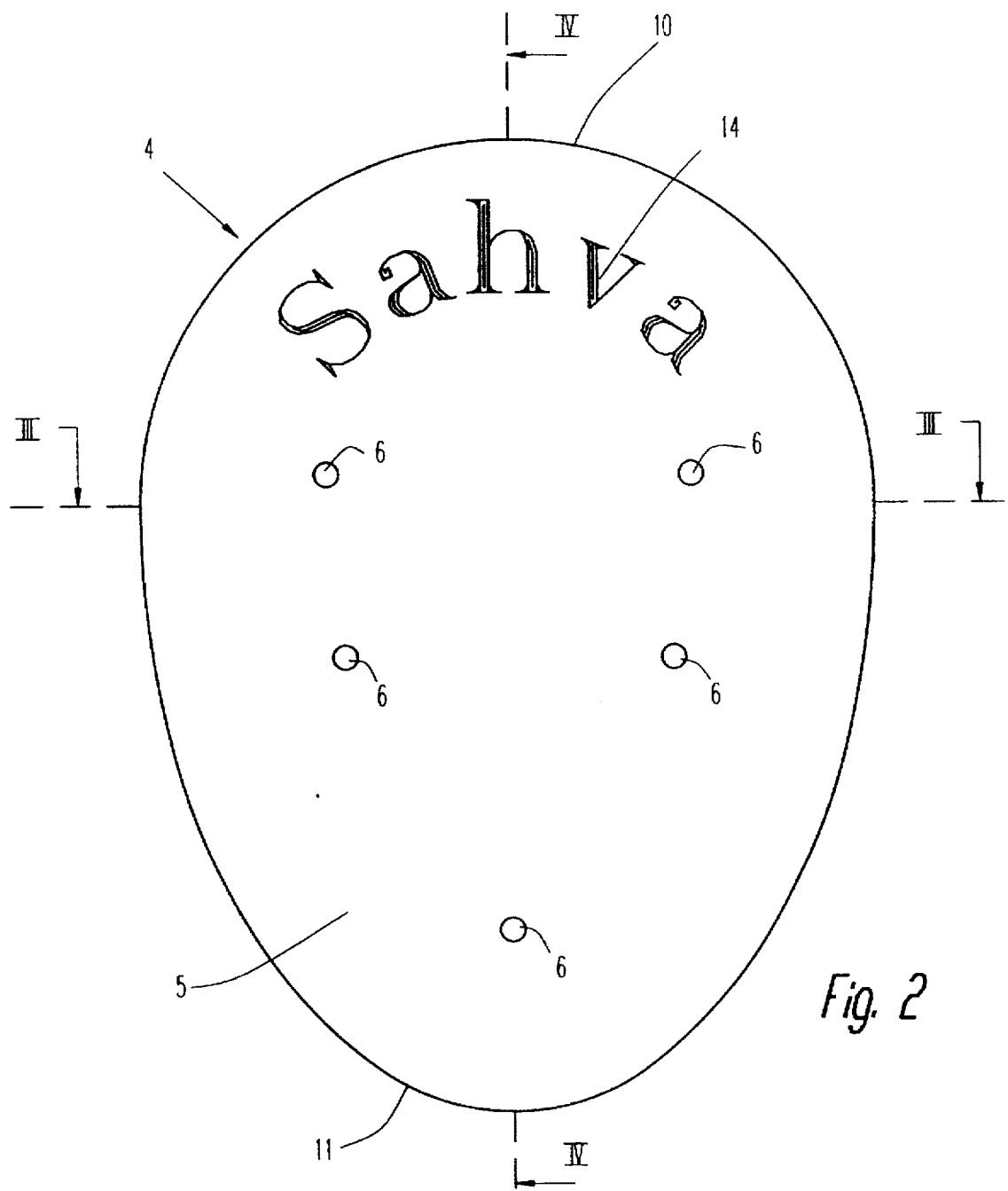
FIG. 2 shows a hip protector as viewed from the convex side.
Figure 3:
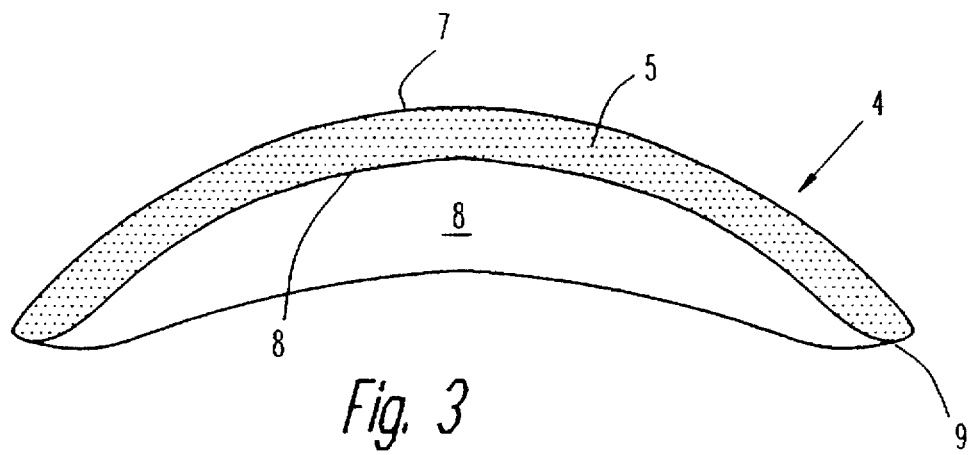
FIG. 3 is a plane section along the line III—III of FIG. 2.
Figure 4:
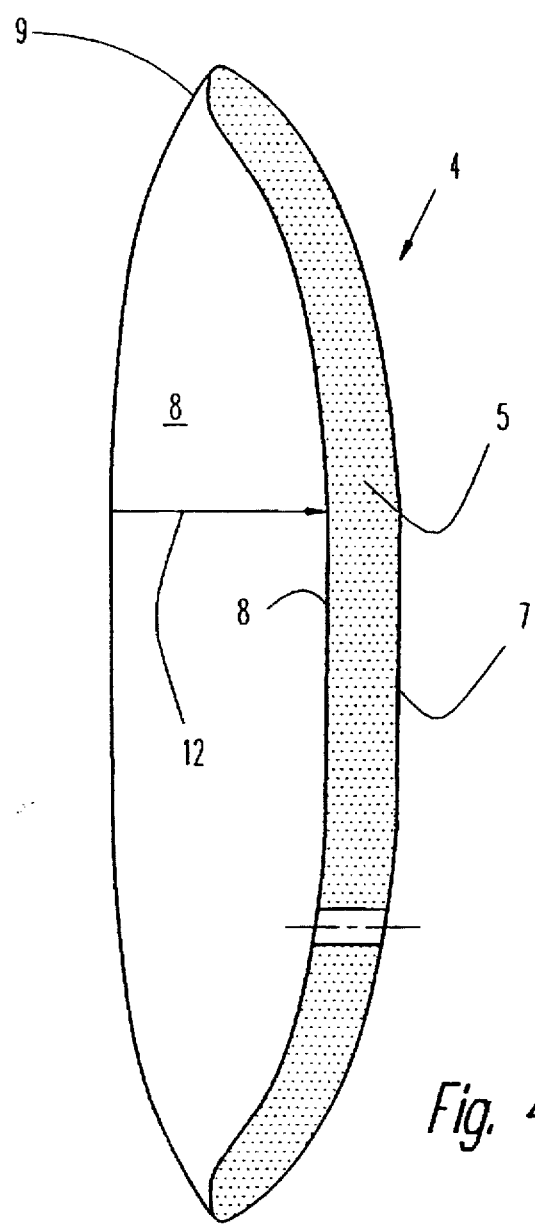
FIG. 4 is a sectional view taken along the line IV—IV of FIG. 2.
Figure 5:
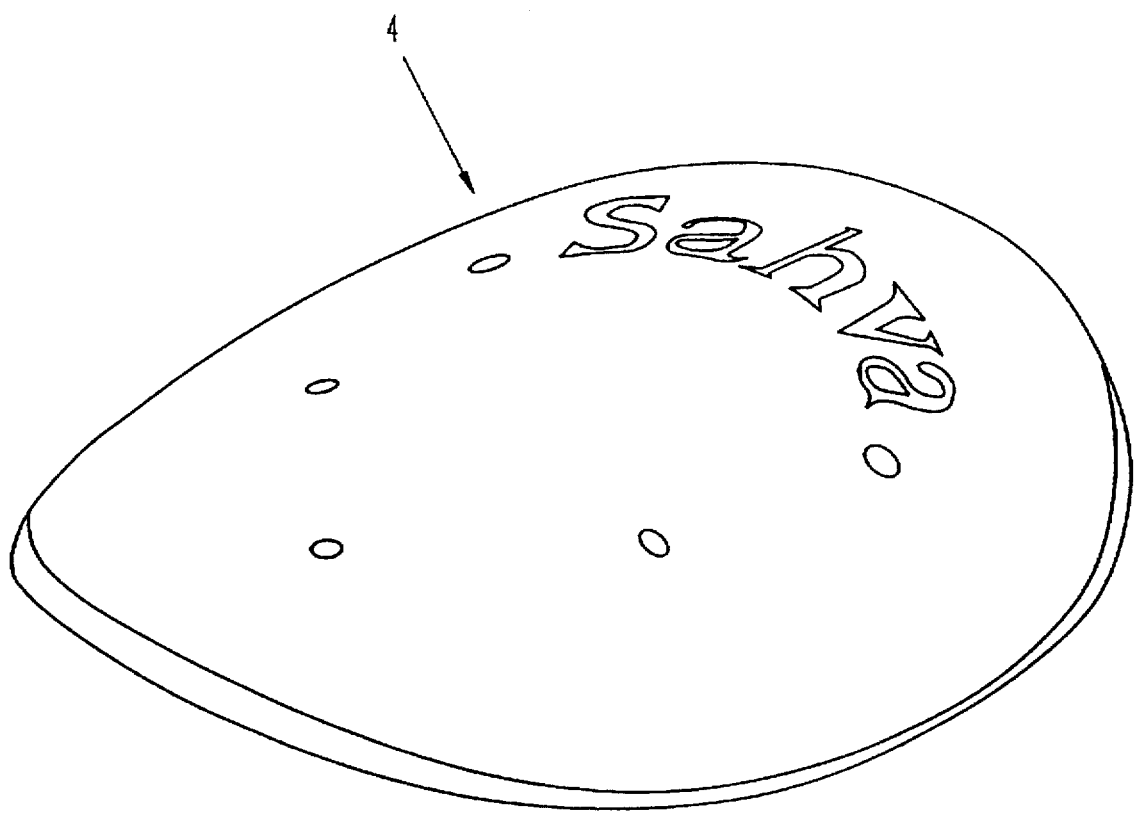
FIG. 5 is a perspective view showing the exterior side of the hip protector.

Thus, this dome-shaped shell 5 is elliptical or oval in plane view and terminating in a slightly obtuse end 11 and a fairly round end 10 (FIG. 2). The hip protector is fitted to the body with said slightly obtuse end 11 facing downward as viewed in FIG. 1.

This shell 5 has a convex surface 7 and a concave surface 8 which faces inward when the protector is fitted to the body. The depth 12 of the dome is of the order of 2.5 to 4.5 cm and preferably about 3.0 cm.

Furthermore, this hip protector has a major diameter of 13 to 18 cm, preferably about 16 cm and a minor diameter of 9 to 14 cm, preferably about 11.5 cm. The thickness of the shell 5 is of the order of 0.5–1.5 cm and preferably about 0.9 cm.

The shell 5 can be produced by the known molding technique using a rigid thermoplastic foam material, such as polypropylene foam, which withstands laundering by boiling. By such technique, it is relatively easy to obtain a shell of closed-cell structure with a grained surface which is comfortable to the user and easy to clean.

For improved user comfort, the hip protector can be provided with a plurality of perforations or apertures 6 in off-center positions distributed at appropriate distances from the rim without reducing the strength of the shell as typically illustrated in FIG. 2.

In the course of manufacture of the shell 5, a literal or decorative motif 14 can be formed, as indicated at 14, on the surface of the shell. The motif not only serves the purpose of ornamentation or identification but also functions as a guide to the user in wearing the hip protector.

Figure 6:
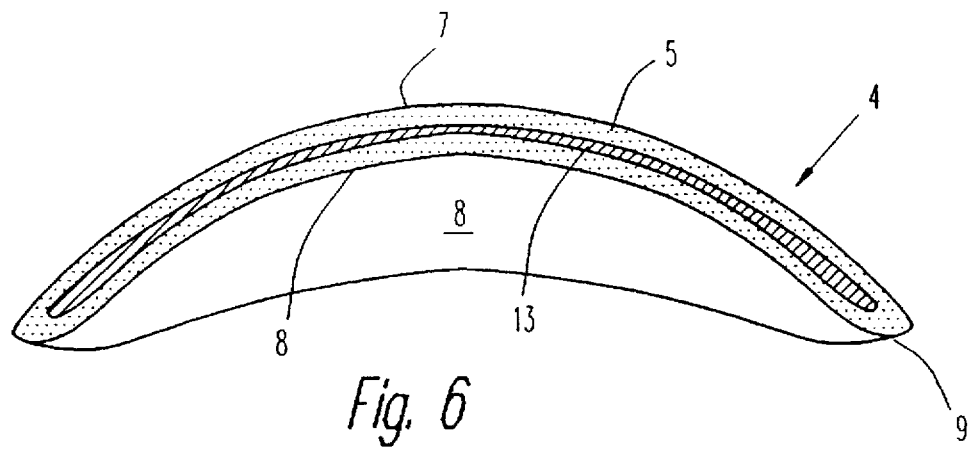
FIG. 6 is a cross-section view corresponding to FIG. 3 of a preferred embodiment.
Figure 7:
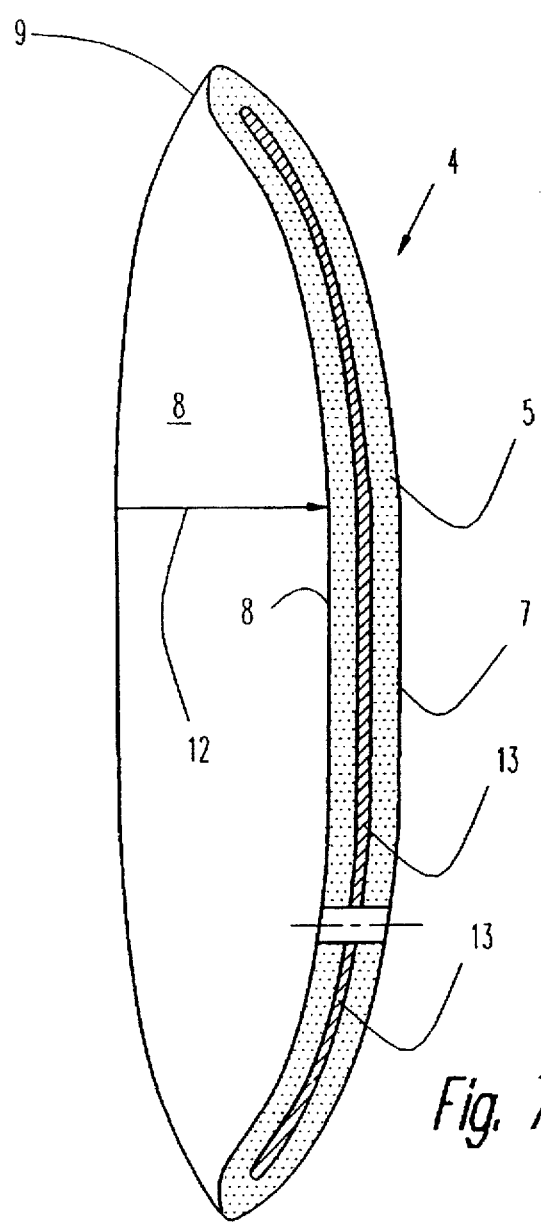
FIG. 7 is a cross-section view corresponding to FIG. 4 of the same preferred embodiment.

FIGS. 6 and 7 show sectional views of an embodiment with markedly improved strength. This dome-shaped hip protector includes a reinforcing core 13. A plurality of core members may be employed, of course. In the illustrated embodiment, the reinforcing core 13 is a member generally conforming to the curvature of the shell and made of a rigid or semi-rigid thermoplastic material, such as polypropylene. The core terminates about 8–15 mm from the rim of the shell 5. The marginal area 9 of the shell, external of said core 13, is relatively flexible, the result being that the hip protector is as comfortable to wear as the protector shown in FIGS. 3 and 4. The reinforcing core 13 is completely concealed. This protector is otherwise similar to the protector shown in FIGS. 2 to 5, for example in size, configuration and surface structure.

What is claimed is:

1. A hip protector for protecting the neck region of the femur of a human body comprising:

a resilient shell having a substantially uniform thickness, a convex side, a concave side and annular outer rim forming a continuously smooth dome shape surface without sharp edges;

a rigid internal core encased by the resilient shell and maintained a distance from the annular outer rim;

the concave side being concave in both the transverse and longitudinal direction, wherein, upon positioning on a human body, the annular outer rim abuts the human body while the inner concave surface is spaced from and precluded from abutting the human body;

the annular outer rim comprises a substantially elliptical configuration having a major diameter which terminates in a generally round end with symmetrical sides and in a slightly obtuse end with symmetrical sides, and a minor diameter;

the resilient shell is made of a closed-cell thermoplastic material such as polypropylene foam;

the core substantially conforms to the shape of the shell member and is made of a rigid thermoplastic material such as polypropylene and completely concealed in said shell; and wherein when properly positioned on the human body, said slightly obtuse end faces downward as attached and is curved to provide a depth of the dome shaped shell member between 2.5 cm and 4.5 cm.

2. The hip protector according to claim 1 wherein said protector is provided with a plurality of apertures extending from said concave side to said convex side and at a distance from the annular outer rim of the shell.

3. The hip protector according to claim 1 wherein the major diameter measures between 13 cm and 18 cm.

4. The hip protector according to claim 3 wherein the major diameter measures 16 cm.

5. The hip protector according to claim 1 wherein the minor diameter measures between 9 cm and 14 cm.

6. The hip protector according to claim 5 wherein the minor diameter measures 11.5 cm.

7. The hip protector according to claim 1 wherein the substantially uniform thickness of the resilient shell measures between 0.5 cm to 1.5 cm.

8. The hip protector according to claim 7 wherein the thickness of the resilient shell measures 0.9 cm.

9. The hip protector according to claim 1 wherein the distance from the annular outer rim to the rigid core is between 0.8 cm and 1.5 cm.

10. The hip protector according to claim 1 wherein the shell includes a grained surface.

11. The hip protector according to claim 1 wherein the depth of the dome is preferably about 3.0 cm.

* * * * *